US00PP22743P2

(12) United States Plant Patent
Hegedus

(10) Patent No.: US PP22,743 P2
(45) Date of Patent: May 22, 2012

(54) JUNIPER PLANT NAMED 'HEGEDUS'

(50) Latin Name: *Juniperus horizontalis*
Varietal Denomination: Hegedus

(75) Inventor: Mark Hegedus, Geneva, OH (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/925,452

(22) Filed: Oct. 21, 2010

(51) Int. Cl.
*A01H 7/00* (2006.01)

(52) U.S. Cl. ..... Plt./214

(58) Field of Classification Search ..... Plt./214
See application file for complete search history.

*Primary Examiner* — June Hwu
(74) *Attorney, Agent, or Firm* — C. A. Whealy

(57) ABSTRACT

A new and distinct cultivar of Juniper plant named 'Hegedus', characterized by its compact and outwardly spreading to prostrate plant form; yellow green-colored developing leaves becoming bright green when fully developed; and foliage that is soft to the touch.

2 Drawing Sheets

Botanical designation: *Juniperus horizontalis*.
Cultivar denomination: 'HEGEDUS'.

BACKGROUND OF THE INVENTION

The present Invention relates to a new and distinct cultivar of Juniper plant, botanically known as *Juniperus horizontalis*, and hereinafter referred to by the name 'Hegedus'.

The new Juniper plant is a naturally-occurring branch mutation of *Juniperus horizontalis* 'Hughes', not patented. The new Juniper plant was discovered and selected by the Inventor on a single plant within a population of plants of 'Hughes' in a controlled greenhouse environment in Geneva, Ohio.

Asexual reproduction of the new Juniper plant by hardwood cuttings in a controlled greenhouse environment in Grand Haven, Mich. has shown that the unique features of this new Juniper plant are stable and reproduced true to type in successive generations.

SUMMARY OF THE INVENTION

Plants of the new Juniper have not been observed under all possible environmental conditions. The phenotype may vary somewhat with variations in environment such as temperature and light intensity without, however, any variance in genotype.

The following traits have been repeatedly observed and are determined to be the unique characteristics of 'Hegedus'. These characteristics in combination distinguish 'Hegedus' as a new and distinct cultivar of Juniper plant:

1. Compact and outwardly spreading to prostrate plant form.
2. Yellow green-colored developing leaves becoming bright green when fully developed.
3. Foliage that is soft to the touch.

Plants of the new Juniper can be compared to plants of the mutation parent, 'Hughes'. Plants of the new Juniper differ primarily from plants of 'Hughes' in the following characteristics:

1. Plants of the new Juniper and 'Hughes' differ in leaf color as plants of 'Hughes' have dark green-colored leaves.
2. Leaves of plants of the new Juniper are softer to the touch than and not as prickly as leaves of plants of 'Hughes'.

Plants of the new Juniper can also be compared to plants of *Juniperus horizontalis* 'Mother Lode', disclosed in U.S. Plant Pat. No. 5,948. Plants of the new Juniper differ primarily from plants of 'Mother Lode' in the following characteristics:

1. Plants of the new Juniper are taller than plants of 'Mother Lode'.
2. Plants of the new Juniper are faster growing than plants of 'Mother Lode'.
3. Plants of the new Juniper are more prostrate than and not as procumbent as plants of 'Mother Lode'.
4. Leaves of plants of the new Juniper are softer to the touch than and not as prickly as leaves of plants of 'Mother Lode'.

BRIEF DESCRIPTION OF THE PHOTOGRAPHS

The accompanying colored photographs illustrate the overall appearance of the new Juniper plant showing the colors as true as it is reasonably possible to obtain in colored reproductions of this type. Colors in the photographs may differ slightly from the color values cited in the detailed botanical description which accurately describe the colors of the new Juniper plant.

The photograph on the first sheet is a side perspective view of a typical plant of 'Hegedus' grown in a container.

The photograph on the second sheet is a top perspective view of a typical plant of 'Hegedus'.

DETAILED BOTANICAL DESCRIPTION

Plants used for the aforementioned photographs and following observations and measurements were grown in Grand Haven, Mich. during the spring and summer in 3-gallon containers in an outdoor nursery in Grand Haven, Mich. Plants were grown under conditions which approximate commercial Juniper plant production. Plants were three years old when the photographs and description were taken. In the following description, color references are made to The Royal Horticultural Society Colour Chart, 1995 Edition, except where general terms of ordinary dictionary significance are used.

Botanical classification: *Juniperus horizontalis* 'Hegedus'.

Parentage: Naturally-occurring branch mutation of *Juniperus horizontalis* 'Hughes', not patented.

Propagation:

*Type.*—By hardwood cuttings.

*Time to initiate roots.*—About three months at 20° C.

*Time to produce a rooted cutting.*—About 200 days at 20° C.

*Root description.*—Fibrous; white to brown in color.

*Rooting habit.*—Freely branching; moderately dense.

Plant description

*Form/growth habit.*—Perennial evergreen shrub; compact and outwardly spreading to prostrate plant habit; moderate growth rate and good plant vigor.

*Branching habit.*—Freely branching with about 28 lateral branches developing per plant.

*Plant height.*—About 30 cm to 40 cm.

*Plant diameter.*—About 100 cm to 200 cm.

*Lateral branch description.*—Length: About 26 cm. Diameter: About 4 mm. Internode length: About 1 cm. Texture: Smooth. Strength: Strong. Orientation: About 45° to 90° from vertical. Color, developing: Close to 151B. Color, mature: Close to 175B.

*Leaf description.*—Arrangement: Flattened, appressed and imbricate; opposite and whorled; simple; sessile. Length: About 5 mm. Width: About 1.5 mm. Shape: Acicular. Apex: Narrowly acute. Base: Cuneate. Margin: Entire. Texture, upper and lower surface: Smooth, glabrous; soft to the touch. Venation pattern: Parallel. Fragrance: Juniper-like. Color: Developing leaves, upper and lower surfaces: Close to 1B. Fully expanded leaves, upper and lower surfaces: Close to 141A; venation, close to 141A.

*Cone description.*—Cone development has not been observed.

Disease/pest resistance: Plants of the new Juniper have not been noted to be resistant to pathogens or pests common to Juniper.

Weather tolerance: Plants of the new Juniper have been observed to be tolerant to drought, rain, wind and temperatures ranging from about −38° C. to about 35° C.

It is claimed:

1. A new and distinct Juniper plant named 'Hegedus' as illustrated and described.

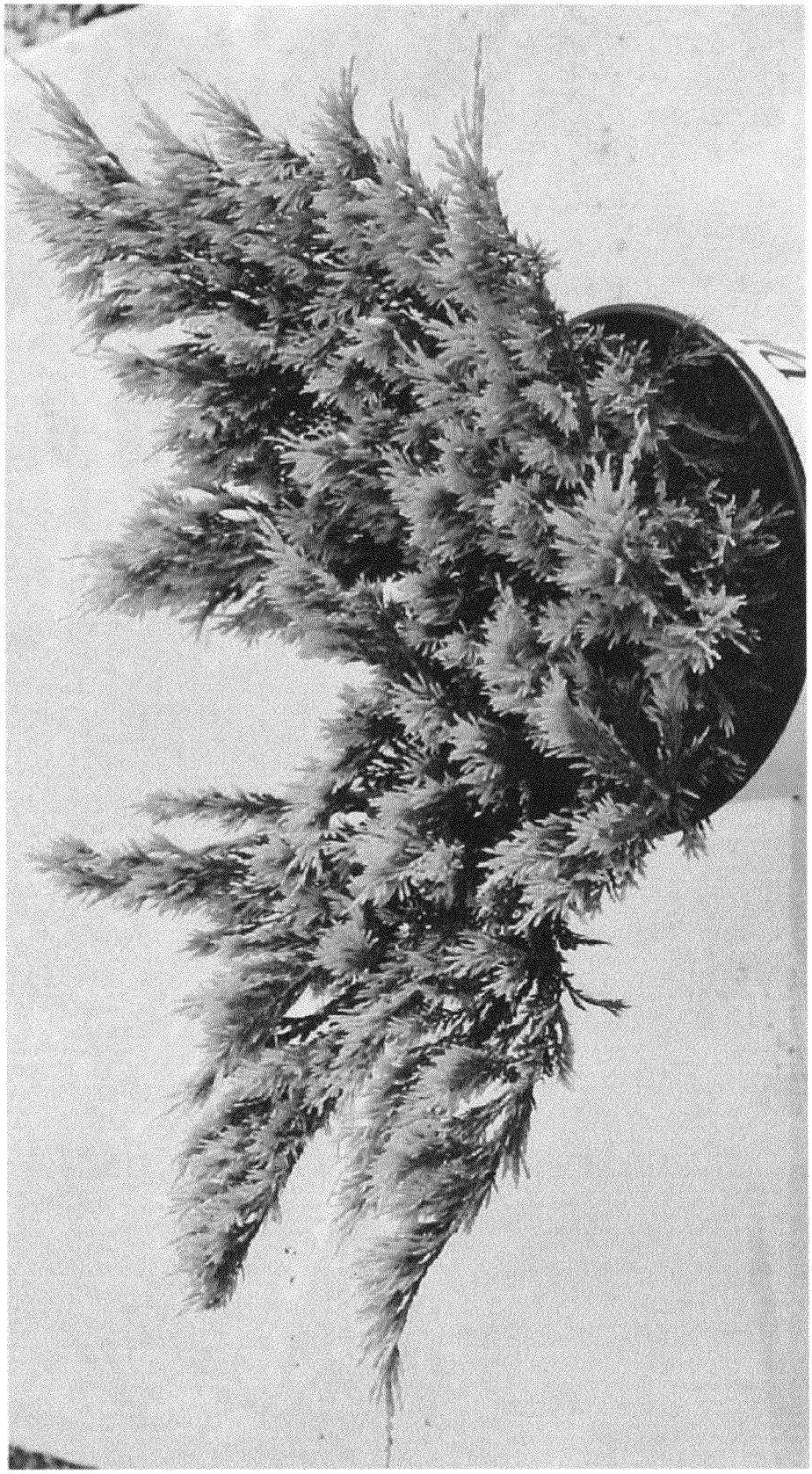

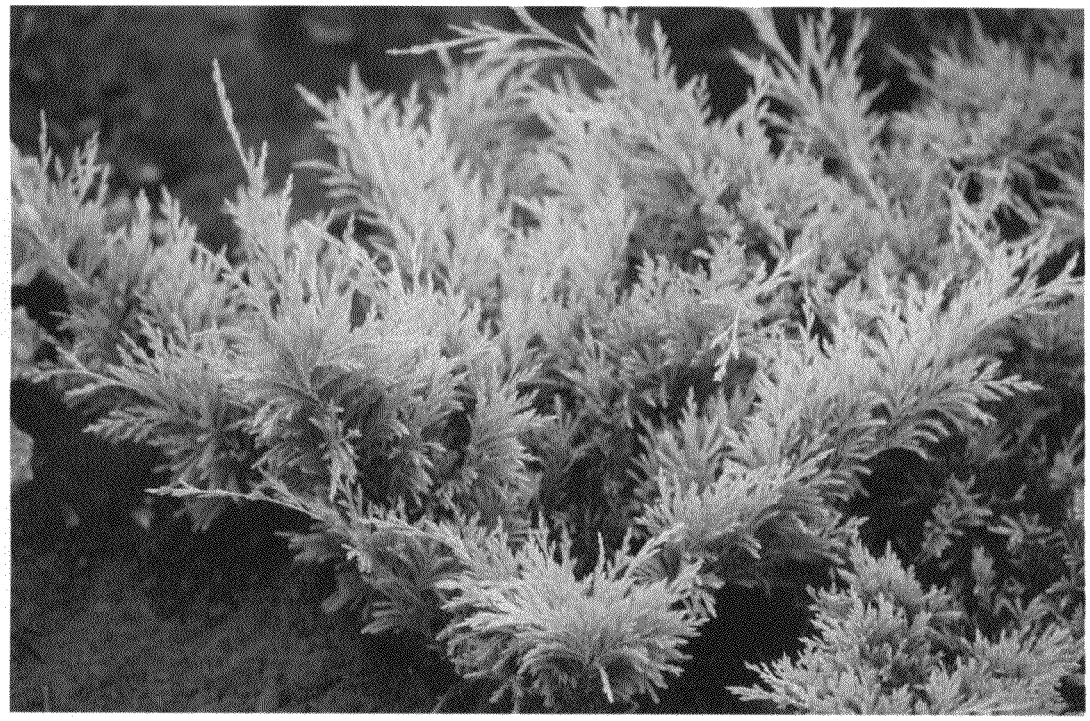

* * * * *